US006779481B2

(12) United States Patent
Kent et al.

(10) Patent No.: US 6,779,481 B2
(45) Date of Patent: Aug. 24, 2004

(54) ELECTRICAL COUPLING BETWEEN CHAMBER PARTS IN ELECTRONIC DEVICE PROCESSING EQUIPMENT

(75) Inventors: Martin A. Kent, Andover, MA (US); Abron Toure, Portland, OR (US); Stephen N. Golovato, Austin, TX (US)

(73) Assignee: Tokyo Electron Limited, Tokyo (JP)

( * ) Notice: Subject to any disclaimer, the term of this patent is extended or adjusted under 35 U.S.C. 154(b) by 98 days.

(21) Appl. No.: 09/789,575

(22) Filed: Feb. 22, 2001

(65) Prior Publication Data

US 2001/0035132 A1 Nov. 1, 2001

(51) Int. Cl.[7] ............................................. C23C 16/509
(52) U.S. Cl. .............................. 118/723 R; 118/723 E; 156/345.43; 156/345.51
(58) Field of Search .............................. 118/712, 715, 118/718, 719, 723 E, 723 ER, 723 I, 723 IR, 723 R, 724; 156/345.24, 345.25, 345.26, 345.27, 345.28, 345.29, 345.34, 345.36, 345.43, 345.44, 345.48; 204/298.02, 298.03, 298.05; 216/67, 69, 71, 76; 219/390, 405

(56) References Cited

U.S. PATENT DOCUMENTS

| 5,518,593 | A | * | 5/1996 | Hosokawa et al. ......... 118/641 |
| 6,057,235 | A | * | 5/2000 | Leiphart et al. ........ 118/723 R |
| 6,120,640 | A | * | 9/2000 | Shih et al. .................. 118/719 |
| 6,159,299 | A | * | 12/2000 | Koai et al. .................. 118/728 |
| 6,221,221 | B1 | * | 4/2001 | Al-Shaikh et al. ....... 118/723 E |
| 6,228,229 | B1 | * | 5/2001 | Raaijmakers et al. .. 204/192.15 |
| 6,251,792 | B1 | * | 6/2001 | Collins et al. ............... 438/729 |
| 6,264,788 | B1 | * | 7/2001 | Tomoyasu et al. .......... 118/500 |
| 6,270,859 | B2 | * | 8/2001 | Zhao et al. ............ 427/255.391 |
| 6,283,060 | B1 | * | 9/2001 | Yamazaki et al. .......... 118/719 |
| 6,364,949 | B1 | * | 4/2002 | Or et al. ...................... 118/715 |
| 6,379,756 | B2 | * | 4/2002 | Komino ........................ 216/67 |

* cited by examiner

*Primary Examiner*—Jeffrie R. Lund
*Assistant Examiner*—Rudy Zervigon
(74) *Attorney, Agent, or Firm*—Oblon, Spivak, McClelland, Maier & Neustadt, P.C.

(57) ABSTRACT

An electrical coupling is provided between chamber parts of electronic device processing equipment (e.g., equipment used for processing semiconductor wafers) to reduce differences in the electrical potential between such parts. The coupling prevents or at least reduces the presence of plasma or excited gases in undesired regions of the process chamber. In illustrated embodiments, the coupling extends from a cover of a vertically movable electrode assembly to the liner of the chamber wall. Although these parts are each respectively coupled to ground, it is believed that differences in the ground path impedances result in these parts having different electrical potentials, and the potential differences can cause plasma or excited gases to be present in undesirable regions of the chamber. These electrical potential differences are suppressed by electrically coupling the parts to thereby prevent or reduce the presence of plasma or excited gases in undesired regions of the chamber. Although in the illustrated embodiments the cover of the electrode assembly is coupled to the chamber liner, the coupling could be utilized to suppress potential differences between other chamber parts.

27 Claims, 2 Drawing Sheets

ELECTRICAL COUPLING BETWEEN CHAMBER PARTS IN ELECTRONIC DEVICE PROCESSING EQUIPMENT

BACKGROUND OF THE INVENTION

1. Field of the Invention

The invention relates to electronic device processing equipment. More particularly, the invention provides an electrical coupling between a fixed chamber part (such as a chamber liner or chamber wall) and a movable chamber part (such as an element of a movable electrode assembly) to reduce differences in the electrical potential of such parts and prevent or reduce the presence of excited gases or plasma in undesired regions of the processing equipment.

2. Discussion of Background

Various types of processing equipment are utilized in the manufacture of electronic devices such as semiconductor devices or panels used in liquid crystal displays. For example, deposition equipment is utilized for depositing films or layers upon a semiconductor wafer. "Etchers" typically utilize a plasma to remove or etch portions of a film or layer from a wafer to form the desired features or devices upon the wafer. Due to the extremely small size of the features formed in semiconductor processing, the processing equipment must be carefully and precisely controlled. The equipment usually includes a "chamber" or enclosed region, within which the environment is controlled for optimal processing of the wafers.

In electronic device processing equipment, electrodes are utilized to control the environment within the process chamber. For example, etchers typically utilize electrodes to excite the process gases into a state known as a "plasma." The plasma performs a process upon the wafer, e.g., to deposit a layer on the wafer or to etch the wafer, and the process gases (and byproducts) are then exhausted from the chamber.

There are various chamber and electrode configurations in electronic device processing equipment. One known plasma etcher arrangement includes parallel upper and lower electrodes. The upper electrode is grounded, and radio frequency power is applied to the lower electrode to strike and maintain a plasma between the upper and lower electrodes. Depending upon the geometry and other factors, the plasma in this type of an arrangement can also be coupled to a grounded chamber wall (and/or the liner of the chamber wall if a liner is provided) such that the upper electrode and chamber wall, in effect, form the ground electrode. Many other process chamber configurations are also known. For example, certain etchers include more than one powered electrode.

Regardless of the particular configuration, the electrodes are extremely important components in controlling the process performed within the chamber. Other components within the chamber are also needed, which are not intended to play a role in striking or maintaining a plasma or otherwise controlling the process to be performed. However, although certain chamber parts are not intended to play a role in controlling the process, an electrical potential difference sometimes can occur between such parts (or between such non-electrode parts and electrode parts). These unintended and undesirable potential differences can have a number of deleterious effects. For example, an unintended potential difference could cause a plasma or excited gases to be present in unintended regions of the chamber. This plasma can adversely effect the plasma (or the control of the plasma) in regions of the chamber in which plasma is intended to be present. For example, the properties and performance of the plasma in the chamber can be affected if the plasma should become coupled to parts in unintended/undesirable regions of the chamber. The unintended/undesired plasma or excited gases could also cause the etching or wear and premature failure of the chamber parts. Moreover, the etching of such parts can generate particles, introducing impurities onto the surface of the wafer. Deposits on the chamber parts can also generate particles when the deposits are subsequently dislodged.

SUMMARY OF THE INVENTION

The present invention provides an arrangement which can reduce the presence of plasma or excited gases in regions of a chamber for which such plasma or gases are not desired or intended. The present invention can also reduce the adverse effects such plasma or gases can cause.

In one form of the invention, an electrical coupling is provided between chamber parts to eliminate or at least reduce differences in the electrical potential between such parts, thereby reducing the possibility that plasma (or excited gases) will be formed, sustained or have undesirable effects. By way of example, in an illustrated embodiment, an improved electrical coupling is provided in a two electrode etcher assembly having a powered movable lower electrode assembly and a ground upper electrode. The movable electrode assembly includes parts which are insulated from the powered electrode, and which are not intended to be powered or to have a potential difference with other grounded parts of the chamber, such as the grounded chamber wall. However, it has been found that potential differences between parts of the lower electrode assembly and the chamber wall can occur, and can result in the presence of excited gases or a plasma in undesirable regions of the chamber. Potential differences can assist in drawing plasma or excited gases created in other regions into the undesirable or unintended regions, or the potential differences could cause the formation of a plasma or excited gases in the undesirable regions. In either case, it has been recognized in accordance with the present invention that, by providing an electrical coupling between the chamber parts, such as parts associated with the movable electrode assembly and parts associated with the chamber wall, the undesirable presence of plasma or excited gases can be prevented or reduced. The terms "plasma or excited gases" are used herein since excited gases can sometimes be present and have characteristics associated with a plasma (e.g., emitting light) although such gases are not always truly a plasma.

In one form of the invention, the electrical coupling extends between a first chamber part which is fixed and a second chamber part which is movable. In the illustrated embodiments, the first chamber part is an unpowered part of a movable lower electrode assembly, and the second chamber part is a chamber liner which lines the wall of the chamber. The electrode assembly is movable so that in an upper or raised position, the lower electrode is properly positioned for processing the wafer. The electrode assembly is lowered when a process is not being performed to allow placement of a wafer upon the electrode or removal of a processed wafer from the electrode. The electrical coupling includes a yieldable portion, such as a flexible portion or spring biased portion, such that the electrical coupling can be urged or biased toward the second or fixed chamber part to ensure contact when the lower electrode assembly is in its raised or operational position. Although the illustrated embodiments provide an electrical coupling between part of a movable electrode assembly and a chamber liner in an etcher having a single powered electrode, as discussed in further detail herein, the invention can be advantageously utilized in various types of electronic device processing equipment and to couple various parts to reduce potential differences which could be present between such parts.

BRIEF DESCRIPTION OF THE DRAWINGS

A more complete understanding of the invention and many of the attendant advantages thereof will become apparent from the following detailed description, particularly when considered in conjunction with the accompanying drawings in which.

DETAILED DESCRIPTION OF THE PREFERRED EMBODIMENTS

Figure 1:
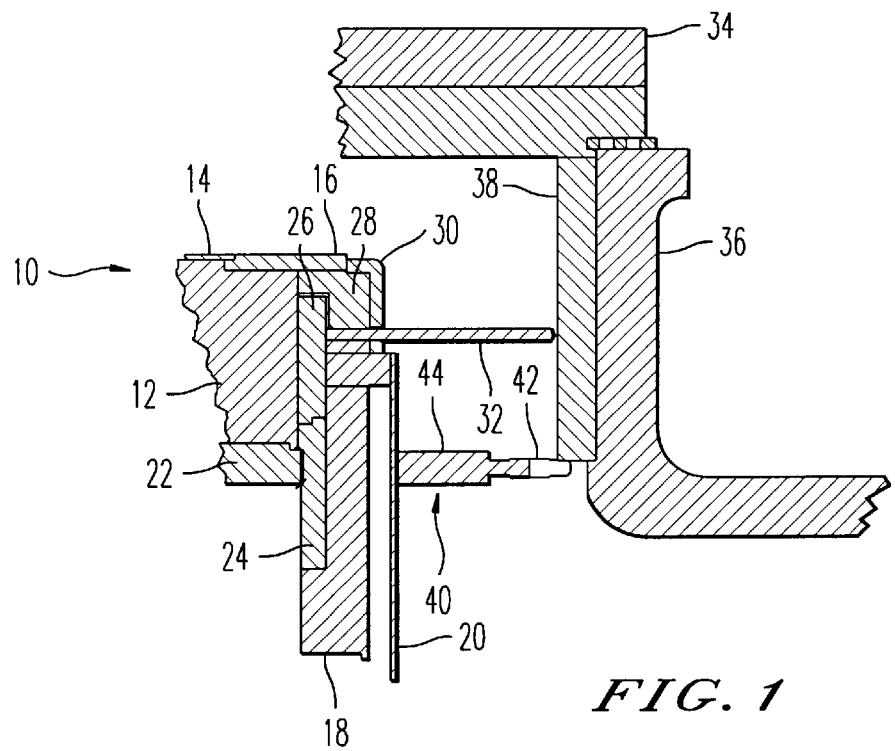
FIG. 1 is a cross-sectional view of a portion of an electronic device processing apparatus depicting an embodiment of the invention.

Referring to the drawings, wherein like reference numerals designate the same or corresponding parts, FIG. 1 depicts a cross-sectional view of a portion of a process chamber to illustrate an embodiment of the invention. The electronic device processing equipment of FIG. 1 is a plasma etcher which includes a powered electrode provided on a movable lower electrode assembly and a ground electrode. However, it is to be understood that the invention is applicable to other types of electronic device processing equipment where it is desirable to improve the plasma confinement, prevent or minimize the presence of plasma or excited gases in undesired regions of the process chamber, or otherwise avoid disadvantageous effects which can occur as a result of potential differences between chamber parts.

The arrangement of FIG. 1 includes a vertically movable lower electrode assembly 10. The movable lower electrode assembly 10 includes a powered electrode 12, upon which a semiconductor wafer 14 is disposed for processing. The part shown at 16 is a focus ring, and is utilized to improve the uniformity of the process to be performed on the wafer. The electrode assembly 10 further includes an a housing 18 and a cover 20 which move with movement of the lower electrode assembly 10. In this arrangement, another cover (not shown) is typically provided and is mounted at a bottom portion of the chamber. This second cover is fixed and partially overlaps with the cover 20 so that the covers together protect the lower electrode assembly. The use of overlapping covers ensures coverage of the electrode assembly despite the fact that the electrode assembly is movable, since the movement of the electrode assembly simply changes the amount of overlap between the two covers. When the electrode assembly 10 is in its lowermost position, the overlap is the greatest. When the electrode assembly 10 is in its uppermost position, the overlap is the smallest. Nevertheless, since there remains an overlap between the two covers when the electrode assembly 10 is in the uppermost position, the covers ensure that the lower electrode assembly is covered. Some etchers include a bellows or flexible covering disposed within the cover 20 to form a barrier about, for example, the drive mechanisms utilized for raising and lowering the electrode assembly 10. For this reason, the cover 20 (and the non-illustrated fixed cover) is also sometimes referred to as a bellows cover. The drive for electrode assembly 10 can be a threaded shaft, hydraulic, pneumatic or any other suitable expedient. As shown at 22, 24, 26, 28 and 30, insulators are provided to insulate various parts of the electrode assembly, such as the housing 18, cover 20 and baffle plate 32, from the powered electrode 12. Movable lower electrode assemblies and cover assemblies therefor are known to those skilled in the art, and therefore, are not described in further detail herein.

The baffle plate 32 is an annular member which extends about the chamber. In the illustrated embodiment, the baffle plate 32 is mounted to the lower electrode assembly for movement therewith. However, it would also be possible to provide a fixedly mounted baffle plate. This plate 32 includes a number of apertures so that exhaust gases can pass from the region above the baffle plate 32 to the region below the baffle plate 32. The gases are then exhausted through an exhaust outlet (not shown) located in the region of the chamber below the baffle 32. A turbo pump is utilized for drawing the gases through the exhaust outlet as is known in the art.

The chamber also includes a chamber lid 34 and a chamber wall 36. Preferably, the chamber wall 36 is lined with a liner 38 so that the liner can be periodically removed for cleaning. In the arrangement of FIG. 1, an upper electrode (not shown) is disposed above and parallel to the lower electrode 14. The upper electrode is mounted to the chamber lid 34 and is grounded. In the FIG. 1 arrangement, the plasma is coupled to the upper and lower electrodes, and it is also coupled to the chamber wall (or the liner of the chamber wall), since the plasma expands out to the chamber wall. Since the chamber wall is also grounded, with the FIG. 1 arrangement, the chamber wall also acts as a ground electrode or part of the ground electrode in combination with the ground electrode mounted to the chamber lid. Since the upper electrode attached to the chamber lid and the chamber wall are both grounded, they are sometimes considered together to constitute a ground electrode. Thus, the FIG. 1 arrangement provides a two electrode assembly in which one of the electrodes is powered and the other is ground, with the area of the ground electrode including the area of the upper electrode and the area of the chamber wall above the baffle plate which is coupled to the plasma.

Although the invention is illustrated in the context of an etcher which includes a powered electrode and a ground electrode with the plasma expanding to the chamber wall, it is to be understood that the present invention is also applicable to arrangements in which more than one powered electrode is provided, as well as arrangements in which the plasma is to be confined so that it does not expand to contact the chamber wall. For example, the present invention could also be utilized in etchers having more than one powered electrode and/or etchers designed such that the plasma is to be confined to the region between parallel upper and lower electrodes. The invention could also be utilized in electronic device processing equipment other than etchers including, for example, deposition equipment. In addition, although the etcher illustrated herein is for processing semiconductor wafers, the invention could also be utilized in equipment for processing devices other than semiconductor wafers such as equipment which processes panels for liquid crystal or flat panel displays.

In the FIG. 1 arrangement, due to the remoteness of the region beneath the baffle plate 32 from the powered electrode and due to the presence of the baffle plate 32, the arrangement is intended to prevent or minimize the presence of plasma or excited gases in the region beneath the baffle plate 32. However, plasma or excited gases have nevertheless been found in the region beneath the baffle plate 32. This plasma or excited gas can be undesirable in a number of respects. First, the parts disposed beneath the baffle plate 32, such as the cover 20, could be adversely effected either by the etching of the parts or by the deposition of process gases or byproducts upon the parts. As a result, the parts could wear prematurely, or particles could be generated (including particles etched from the chamber parts and/or particles from deposits on such parts). In addition, the presence of plasma in an unintended or undesirable region could also affect the plasma in the intended regions, and thereby affect the process to be performed upon the wafer.

In accordance with one aspect of the invention, it has been recognized that the presence of plasma or excited gases can be prevented or reduced by reducing the potential difference between parts within the chamber. Although in the FIG. 1 arrangement, the housing 18 and cover 20 of the lower electrode assembly 10 are grounded and the chamber wall is also grounded, it has been found that potential differences can nevertheless be present between grounded parts such as the cover 20 and the chamber wall 36 or chamber liner 38. It is believed that such potential differences could be the result of differences in the ground path impedances. In accordance with the invention, it has been recognized that, by providing an electrical coupling between these parts, the potential difference is suppressed, and the presence of plasma or excited gases in that region is prevented or reduced.

One difficulty in coupling the chamber parts is that the lower electrode assembly is movable while the chamber wall and chamber liner are fixed. The electrode assembly 10 is movable so that, in a first or raised position, the electrode is properly positioned for etching or other processing of the wafer 14. In the raised or operational position, the lower electrode is positioned so that the spacing (often referred to as the "gap" spacing) between the lower electrode 12 and the upper electrode mounted to the lid 34 is optimal for the process or recipe being performed. This gap spacing can vary depending upon the process. In addition, a different gap spacing is sometimes utilized for performing a cleaning operation. As is known in the art, when the electrode 10 is lowered to a second position or non-operational position, the electrode assembly 10 is properly aligned with a gate opening of the chamber through which wafers are transported, so that a processed wafer can be removed from the lower electrode 12 and a new wafer can be placed upon the lower electrode 12.

In accordance with the invention, the arrangement of FIG. 1 includes an electrical coupling 40 between the cover 20 and the chamber wall, and more particularly to the liner 38 of the chamber wall. To ensure a good contact between the electrical coupling and the liner 38, the coupling includes a spring contact or flexible contact member 42 which is mounted upon a rigid finger or arm 44. This spring contact can be provided, as shown in FIG. 1, as a loop of aluminum ribbon 42 disposed upon the end of the finger or arm 44. The arm 44 is mounted to the cover 20 such that when the electrode assembly 10 is in the first or raised position (or, in other words, the operational position), the contact member 42 is biased or urged against the chamber liner 38 as shown in FIG. 1. It is to be understood that, although in the illustrated embodiments the electrical coupling contacts the chamber liner 38, the coupling could also be shaped or positioned so that it directly contacts the chamber wall 36 in lieu of, or in addition to, contacting the chamber liner 38. Typically, chamber parts such as the chamber liner and/or chamber wall are anodized aluminum. To ensure a good contact, it is preferable to have the electrical coupling 40 contact the fixed part (whether it be the liner and/or the wall) at a location which does not have an anodized surface. This can be more easily accomplished in the manufacture of the chamber liner, particularly if the electrical coupling is to be added on a retrofit basis, since the replaceable chamber liner 38 can be manufactured such that the contact location (i.e., the location at which the electrical coupling contacts the chamber liner) does not have an anodized surface or the anodized surface can be removed. Thus, although it is possible within the scope of the invention to have the electrical coupling contact the chamber wall or other parts, it is presently preferred to have the electrical coupling contact the chamber liner. When the electrode assembly is lowered to a second or non-operational position, the electrical coupling 40 is removed from contact with the chamber liner 38, however since the lower electrode is not powered and a process is not being performed upon a wafer when the electrode assembly is in its lowermost position, this contact is no longer needed. When the electrode assembly 10 is raised, the contact is reestablished, and the fact that the coupling 40 is yieldable or includes a spring contact (via the elasticity of the loop of aluminum ribbon, ribbon in the FIG. 1 embodiment) ensures that a good contact is established.

Alternate arrangements (i.e., other than the yieldable or flexible aluminum ribbon contact 42) are possible to ensure a good coupling when the electrode assembly is in the first or operational position. For example, a yieldable or spring biased contact can be provided by mounting a tip or finger end of the coupling 40 to the arm 44 with a leaf spring, by providing a wire or mesh brush coupling as the contact member at the end of the arm 44, or by other suitable expedients. Depending upon the coupling utilized, the mounting arrangements are preferably also capable of accommodating for at least some variation in gap spacings between the lower electrode 14 and the upper electrode. Alternately, the coupling could be adjustably mounted upon the cover 20 to allow for any needed adjustments for changes in the gap spacing. The electrical coupling 40 provides a good rf coupling between the cover 20 and chamber liner 38. Although the coupling 40 is preferably formed of aluminum, other conductive materials could also be used. In the arrangements shown, the coupling 40 is fixed to the cover 20, for example, by welding. Although the embodiments herein mount the electrical coupling 40 to the movable chamber part with the coupling urged or biased into contact with the fixed chamber part, it would also be possible to mount the coupling to the fixed chamber part, with the coupling urged against the movable chamber part. For example, the coupling 40 could be mounted to the chamber liner or chamber wall with a brush contact or other type of spring biased contact member urged against the cover 20. However, if the contact member is biased against the movable chamber part, a sliding contact relationship is present during movement of the movable part, which could be disadvantageous from a particle generation standpoint. Accordingly, it is presently preferred to mount the electrical coupling to the movable chamber part (cover 20 in the illustrated embodiment).

Figure 2:
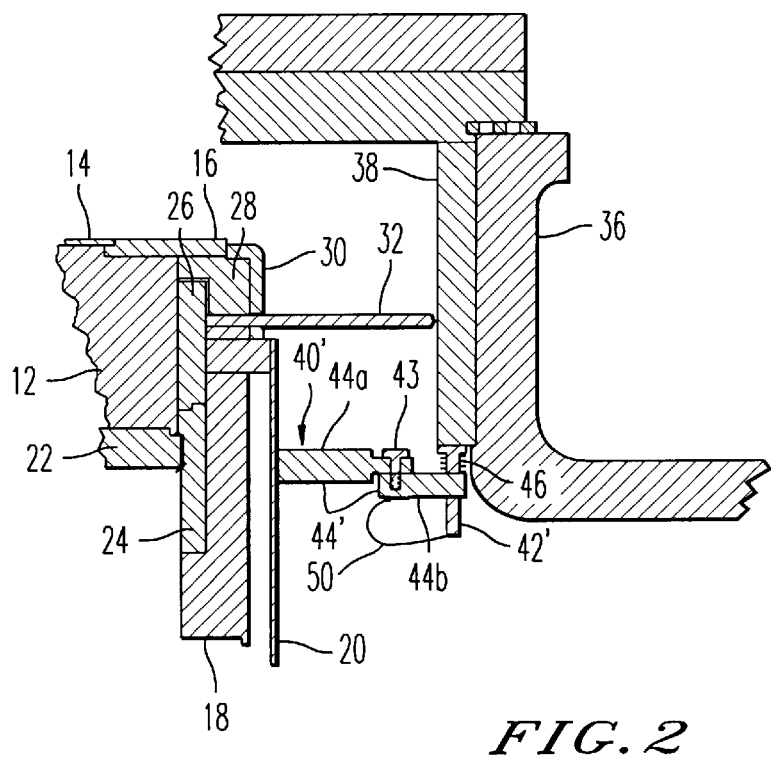
FIG. 2 is a cross-sectional view depicting another embodiment of the invention.

FIG. 2 depicts an alternate embodiment for providing an electrical coupling between the cover 20 and the liner 38. In this arrangement, a contact member 42' is provided in the form of a plunger 42' which is slidably mounted in an aperture of the arm 44'. The arm 44' in the FIG. 2 arrangement includes two pieces 44a, 44b connected by a fastener 43, however the number of pieces which make up the arm can vary in either the FIG. 1 or the FIG. 2 arrangement as could the manner in which the arm parts are connected (e.g., welding could be utilized in conjunction with or in lieu of a fastener). The plunger or contact member 42' is biased with a spring 46 so that the contact member 42' is urged in contact with the chamber liner 38 when the electrode assembly is in its raised or operational position. Since the plunger is slidably received within the arm part 44b, a good electrical contact might not be established between the contact member 42' and the arm part 44b. Such contact could be poor since it is undesirable to have a tight sliding contact in that particles could be generated. In addition, a bushing could optionally be provided in the aperture within which the contact member 42' is slidably received (for a better sliding mount and to avoid particle generation), and such a bushing could also result in a poor electrical coupling between the plunger and the arm 44' via the inner surface of the aperture. Accordingly, an additional electrical connection can be provided by a wire or ribbon 50 which extends from the plunger 42' to the arm 44'. In the embodiment shown, the wire or ribbon 50 extends from the contact member 42' to the arm part 44b. However, the additional electrical coupling 50 could alternately extend to the arm part 44a, or to the part to which the arm 44' is mounted, i.e., the cover 20 in the FIG. 2 embodiment.

Figure 3:
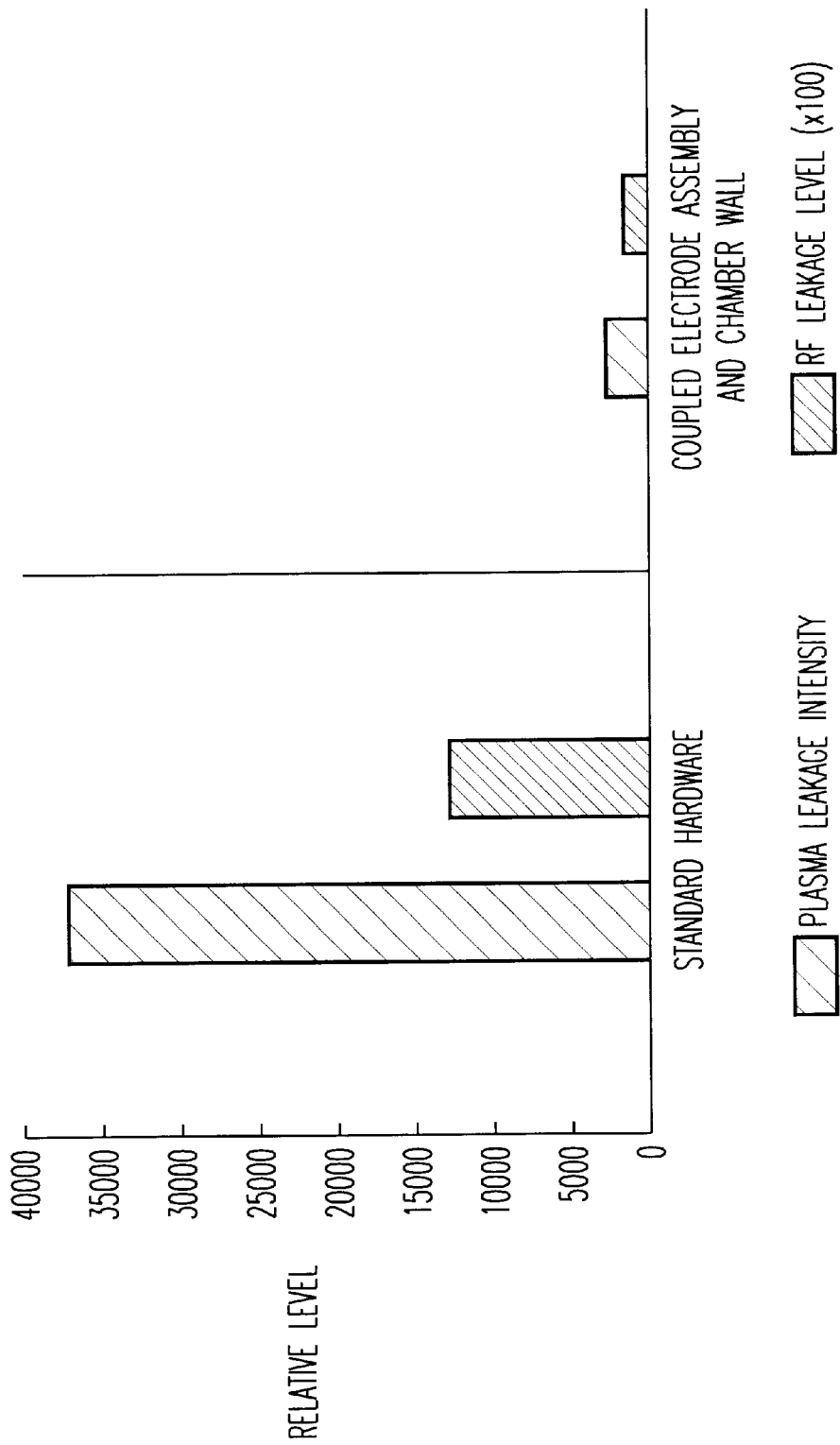
FIG. 3 is a graph depicting advantageous results achieved by the invention.

FIG. 3 depicts the advantageous results achieved by the coupling of the invention. The left pair of bar graphs of FIG. 3 correspond to the results achieved with the standard hardware, i.e., with no coupling between the chamber parts, while the right pair of bar graphs illustrate the results achieved utilizing the coupling between the cover of the electrode assembly and the chamber liner. For each pair of graphs, the left bar graph corresponds to the intensity of the plasma or excited gas found to be present in the region beneath the baffle plate as measured by the intensity of light observed through a sight glass window extending through the chamber wall in that region of the chamber. (As noted earlier, light can be emitted if a plasma or excited gases are present.) As can be seen, the light intensity decreased by a factor of almost 10 utilizing the advantageous electrical coupling of the invention. The right bar graph of each pair illustrates the RF leakage level in the same region as measured by a probe extending through the same sight port. As shown in FIG. 3, the RF voltage present was also significantly reduced by coupling the cover of the electrode assembly and the chamber liner. The data of FIG. 3 demonstrates that, with the invention, the plasma or excited gases are better confined to regions of the chamber the plasma or excited gases are intended to be present. The data shown in FIG. 3 is for comparison purposes to demonstrate relative differences, and therefore, the x-axis is unitless.

As should be apparent from the foregoing, the present invention provides an advantageous coupling between chamber parts to prevent or minimize the presence of plasma or excited gases in unintended and undesired regions of a process chamber, such that the plasma is better confined to the intended regions. As noted earlier, although the illustrated embodiments depict this coupling in an etcher for semiconductor devices, the invention is also applicable to other types of electronic device processing equipment. In addition, although a single coupling is depicted in the illustrated embodiments, it is also to be understood that a plurality of such couplings could be provided spaced about the periphery of the chamber. Further, although the illustrated embodiments provide the coupling between the cover of a movable lower electrode assembly and a chamber wall or wall liner, the coupling could also advantageously be provided between other chamber parts. For example, such a coupling could be provided between a baffle plate 32 and the chamber liner or chamber wall, and obviously the size and shape of the coupling could vary depending upon the parts being coupled. As a further example, the coupling could be provided between a portion of the housing of the lower electrode assembly (e.g., in an arrangement where a cover was not provided or was provided at a different location so that a portion of the housing is exposed) to couple the housing of the lower electrode assembly to the chamber liner or chamber wall. Further, other types of processing equipment could include other types of chamber parts which would benefit from their coupling in order to reduce or eliminate potential differences between the parts which, in accordance with the invention, it has been recognized as resulting in the ability to prevent or reduce the presence of plasma or excited gases in undesired regions of a process chamber.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. An electronic device processing apparatus comprising:
   (a) a chamber within which electronic devices are processed;
   (b) a fixed chamber part;
   (c) a movable chamber part;
   (d) an electrical coupling mounted to one of said fixed chamber part and said movable chamber part, and wherein said electrical coupling contacts the other of said fixed chamber part and said movable chamber part when said movable chamber part is in said first position;
   wherein said electrical coupling includes a yieldable member, and wherein said yieldable member comprises a spring biased contact member which contacts said fixed chamber part when said movable chamber part is in said first position.

2. An electronic device processing apparatus as recite in claim 1, wherein said electrical coupling is mounted to said movable chamber part and moves with said movable chamber part.

3. An electronic device processing apparatus as recited in claim 2, wherein said electrical coupling does not contact said fixed chamber part when said movable chamber part is in said second position.

4. An electronic device processing apparatus as recited in claim 2, wherein said movable chamber part is part of a movable electrode assembly.

5. An electronic device processing apparatus as recited in claim 4, wherein said fixed chamber part includes at least one of: (a) a chamber liner, and (b) a chamber wall.

6. An electronic device processing apparatus as recited in claim 5, wherein said fixed chamber part comprises anodized aluminum.

7. An electronic device processing apparatus as recited in claim 6, wherein said electrical coupling contacts said fixed chamber part at a location which does not have an anodized surface.

8. An electronic device processing apparatus comprising:
   (a) a chamber within which electronic devices are processed;
   (b) a fixed chamber part;
   (c) a movable chamber part which is movable between at least first and second positions;
   (d) an electrical coupling mounted to one of said fixed chamber part and said movable chamber part, and wherein said electrical coupling contacts the other of said fixed chamber part and said movable chamber part when said movable chamber part is in said first position, wherein said electrical coupling comprises:
(i) an arm connected to said one of said fixed chamber part and said movable chamber part, said arm including an aperture;
(ii) a contact member slidably disposed in said aperture; and
(iii) a spring which urges said contact member toward said other of said fixed chamber part and said movable chamber part such that said spring holds said contact member in contact with said other of said fixed chamber part and said movable chamber part when said movable chamber part is in said first position.

9. An electronic device processing apparatus as recited in claim 8, wherein said movable chamber part is a part of a movable lower electrode assembly.

10. An electronic device processing apparatus as recited in claim 9, wherein said movable lower electrode assembly includes a powered lower electrode, and wherein said movable chamber part is insulated from said powered lower electrode.

11. An electronic device processing apparatus as recited in claim 10, wherein said electrical coupling is mounted to said movable chamber part, and wherein said fixed chamber part comprises anodized aluminum, and further wherein said electrical coupling contacts said fixed chamber part at a location which does not have an anodized surface.

12. An electronic device processing apparatus as recited in claim 10, wherein said movable chamber part is a cover of said movable lower electrode assembly.

13. An electronic device processing apparatus as recited in claim 12, wherein said fixed chamber part is a chamber liner.

14. An electronic device processing apparatus comprising:
(a) a chamber within which electronic devices are processed;
(b) a powered electrode;
(c) a first chamber part;
(d) at least one insulator disposed between said powered electrode and said first chamber part;
(e) a second chamber part which is spaced from said first chamber part; and
(f) an electrical coupling which extends between said first chamber part and said second chamber part and which electrically couples said first chamber part and said second chamber part;
wherein said first chamber part is movable between first and second positions, and wherein said second chamber part is fixed, and further wherein said electrical coupling is mounted to said first chamber part, and wherein said electrical coupling contacts said second chamber part when said first chamber part is in said first position, and further wherein said electrical coupling is spaced from said second chamber part when said first chamber part is in said second position.

15. An electronic device processing apparatus as recited in claim 14, further including spring bias means for urging at least a portion of said electrical coupling against said second chamber part when said first chamber part is in said first position.

16. An electronic device processing apparatus as recited in claim 14, wherein said chamber includes a movable electrode assembly, and wherein the powered electrode is part of said movable electrode assembly, and further wherein said first chamber part is also part of said movable electrode assembly.

17. An electronic device processing apparatus as recited in claim 16, wherein said second chamber part comprises one of: (a) a chamber liner, and (b) a chamber wall.

18. An electronic device processing apparatus as recited in claim 16, further including spring bias means for urging at least a portion of said electrical coupling against said second chamber part when said movable electrode assembly is in said first position.

19. An electronic device processing apparatus as recited in claim 16, wherein said powered electrode is a lower electrode.

20. An electronic device processing apparatus as recited in claim 19, wherein said first chamber part is a cover for said movable electrode assembly.

21. An electronic device processing apparatus as recited in claim 19, wherein said second chamber part comprises one of: (a) a chamber liner, and (b) a chamber wall.

22. An electronic device processing apparatus as recited in claim 14, wherein said apparatus includes a baffle plate, and further wherein said electrical coupling is disposed below said baffle plate.

23. An electronic device processing apparatus comprising:
(a) a chamber within which electronic devices are processed;
(b) a powered electrode;
(c) a first chamber part;
(d) at least one insulator disposed between said powered electrode and said first chamber part;
(e) a second chamber part which is spaced from said first chamber part;
(f) an electrical coupling which extends between said first chamber part and said second chamber part and which electrically couples said first chamber part and said second chamber part;
(g) a baffle plate disposed in said chamber, and wherein said electrical coupling is disposed below said baffle plate and extends from said first chamber part at a location below said baffle plate to said second chamber part at a location below said baffle plate; and
(h) wherein said processing apparatus includes a movable electrode assembly that is movable between first and second positions, and wherein said electrical coupling is mounted to said first chamber part, and further wherein said electrical coupling contacts said second chamber part when said movable electrode assembly is in said first position and said electrical coupling is spaced from said second chamber part when said movable electrode assembly is in said second position.

24. An electronic device processing apparatus as recited in claim 23, wherein said first chamber part is a cover for the movable electrode assembly and wherein said powered electrode is part of said movable electrode assembly.

25. An electronic device processing apparatus as recited in claim 24, wherein said second chamber part is a chamber wall.

26. An electronic device processing apparatus as recited in claim 24, wherein said apparatus includes a chamber wall, and wherein said second chamber part is a liner which lines at least a portion of said chamber wall.

27. An electronic device processing apparatus as recited in claim 23, wherein said apparatus includes a chamber wall, and wherein said second chamber part is a liner which lines at least a portion of said chamber wall.

* * * * *